US008152694B2

(12) United States Patent
Srinivasan et al.

(10) Patent No.: US 8,152,694 B2
(45) Date of Patent: Apr. 10, 2012

(54) ACTIVITY MONITORING DEVICE AND METHOD

(75) Inventors: Soundararajan Srinivasan, Munhall, PA (US); Aca Gacic, Pittsburgh, PA (US); Raghu Kiran Ganti, Champaign, IL (US)

(73) Assignee: Robert Bosch GmbH, Stuttgart (DE)

( * ) Notice: Subject to any disclaimer, the term of this patent is extended or adjusted under 35 U.S.C. 154(b) by 348 days.

(21) Appl. No.: 12/404,611

(22) Filed: Mar. 16, 2009

(65) Prior Publication Data

US 2010/0234693 A1 Sep. 16, 2010

(51) Int. Cl.
*A63B 71/00* (2006.01)

(52) U.S. Cl. .................... 482/8; 482/1; 600/595

(58) Field of Classification Search ............ 600/587, 600/595; 482/1, 8–9; 128/920, 921
See application file for complete search history.

(56) References Cited

U.S. PATENT DOCUMENTS

| 6,045,513 | A | 4/2000 | Stone et al. |
| 6,513,532 | B2 * | 2/2003 | Mault et al. ................ 600/595 |
| 7,020,508 | B2 * | 3/2006 | Stivoric et al. ............. 600/390 |
| 7,036,094 | B1 * | 4/2006 | Cohen et al. ............... 715/863 |
| 7,107,180 | B2 * | 9/2006 | Karason ...................... 702/160 |
| 7,210,240 | B2 | 5/2007 | Townsend et al. |
| 7,321,854 | B2 * | 1/2008 | Sharma et al. ............. 704/243 |
| 7,373,820 | B1 * | 5/2008 | James ............................ 73/488 |
| 2002/0170193 | A1 | 11/2002 | Townsend et al. ............ 33/512 |
| 2005/0234310 | A1 * | 10/2005 | Alwan et al. ................ 600/300 |
| 2005/0240086 | A1 * | 10/2005 | Akay .......................... 600/300 |
| 2007/0169364 | A1 | 7/2007 | Townsend et al. |
| 2008/0012701 | A1 * | 1/2008 | Kass et al. ................. 340/539.11 |
| 2008/0082323 | A1 * | 4/2008 | Bai et al. ..................... 704/214 |
| 2008/0146892 | A1 | 6/2008 | Leboeuf et al. |
| 2009/0244309 | A1 * | 10/2009 | Maison et al. ............ 348/222.1 |
| 2010/0030119 | A1 * | 2/2010 | McNames et al. ........... 600/595 |
| 2010/0174674 | A1 * | 7/2010 | Unuma et al. ................. 706/54 |
| 2010/0235341 | A1 * | 9/2010 | Bennett ....................... 707/706 |
| 2011/0054870 | A1 * | 3/2011 | Dariush et al. ................ 703/11 |

OTHER PUBLICATIONS

Miluzzo et al., Sensing Meets Mobile Social Networks: The Design, Implementation and Evaluation of the CenceMe Application; Proc. of SenSys; Nov. 2008; pp. 337-350 (14 pages).
Siewiorek et al., SenSay: A Context-Aware Mobile Phone, IEEE Computer Society, 2003, (2 pages).
Stikic et al., ADL Recognition Based on the Combination of RFID and Accelerometer Sensing, Proceedings of Pervasive Health, 2008, (6 pages).

(Continued)

*Primary Examiner* — Loan Thanh
*Assistant Examiner* — Sundhara Ganesan
(74) *Attorney, Agent, or Firm* — Maginot, Moore & Beck

(57) ABSTRACT

A physical activity monitoring method and system in one embodiment includes a communications network, a wearable sensor device configured to generate physiologic data associated with a sensed physiologic condition of a wearer, and to generate audio context data associated with a sensed audio context of the wearer, and to form a communication link with the communications network, a memory for storing the physiologic data and the audio context data, a computer and a computer program executed by the computer, wherein the computer program comprises computer instructions for rendering activity data associated with the physiologic data and the audio context data, and a user interface operably connected to the computer for rendering the activity data.

20 Claims, 12 Drawing Sheets

OTHER PUBLICATIONS

Philipose et al., Inferring Activities from Interactions with Objects; Pervasive Computing; 2004, pp. 10-17 (8 pages).

Tacconi, D., Mayora, O., Lukowicz, P., Arnrich, B., Troster, G., Haring, C.: "On the feasibiity of using activity recognition and context aware interaction to support early diagnosis of bipolar disorder" In: Ubiwell Ubicomp Workshop 2007, XP002589082, p. 1-p. 4 (4 pages).

Ward J A et al: "Activity recognition of assembly tasks using body-worn microphones ancd accelerometers" IEEE Transactions on Pattern Analysis and Machine Intelligence IEEE Comput. Soc USA, vol. 28, No. 10, Oct. 2006, XP002589083, ISSN: 0162-8828, p. 1553-p. 1567 (15 pages).

International Search Report in corresponding PCT Application (i.e., PCT/US2010/026530), mailed Jul. 15, 2010 (4 pages).

* cited by examiner

ACTIVITY MONITORING DEVICE AND METHOD

FIELD

This invention relates to wearable monitoring devices.

BACKGROUND

Physical fitness has been a growing concern for both the government as well as the health care industry due to the decline in the time spent on physical activities by both young teens as well as older adults. Self monitoring of individuals has proven to be helpful in increasing awareness of individuals to their activity habits. By way of example, self-monitoring of sugar levels by a diabetic helps the diabetic to modify eating habits leading to a healthier lifestyle.

Self-monitoring and precisely quantizing physical activity has also proven to be important in disease management of patients with chronic diseases, many of which have become highly prevalent in the western world. A plethora of different devices and applications have surfaced to serve the needs of the community ranging from simple pedometers to complex web-based tracking programs.

Wearable devices and sensors have seen a tremendous global growth in a range of applications including monitoring physical activity. Several physical activity monitoring systems incorporate a variety of sensors which store the sensor data on a wearable device and process the data offline in a separate device. Typically, the known systems require proactive or reactive specification of the physical actions performed by the user. Additionally, while known systems are able, to some extent, to ascertain the general nature of activity that an individual is undertaking, the systems are not able to provide detailed information as to the context in which the activity is being undertaken.

Micro-electromechanical system (MEMS) sensors, which have a small form factor and exhibit low power consumption without compromising on performance, have received increased attention for incorporation into wearable sensors. For example, inertial MEMS sensors such as accelerometers can be placed into an easy and light portable device to be worn by users.

Accordingly, there is a need for smarter applications and wearable devices that track, record and report physical activities of the wearer. It would be beneficial if such a device did not require user intervention during the course of the activity. A further need exists for such a system that can deduce the nature of the physical activity. A system which performed physical activity monitoring while providing information regarding the context of the activity would be beneficial.

SUMMARY

A physical activity monitoring method and system in one embodiment includes a communications network, a wearable sensor device configured to generate physiologic data associated with a sensed physiologic condition of a wearer, and to generate audio context data associated with a sensed audio context of the wearer, and to form a communication link with the communications network, a memory for storing the physiologic data and the audio context data, a computer and a computer program executed by the computer, wherein the computer program comprises computer instructions for rendering activity data associated with the physiologic data and the audio context data, and a user interface operably connected to the computer for rendering the activity data.

In accordance with another embodiment, a method of displaying data associated with physical activities includes storing an activity inference engine, generating physiologic data associated with a sensed physiologic condition of the wearer during an activity, generating context data associated with a sensed audio context of the wearer during the activity, using the stored activity inference engine to determine the nature of the activity based upon the physiologic data and the context data, and displaying first data associated with the sensed physiologic data and second data associated with the determined nature of the activity.

In yet another embodiment, a method of monitoring physical activity includes attaching a sensor to a wearer, activating the sensor, generating physiologic data associated with a sensed physiologic condition of the wearer during a wearer activity, generating audio context data associated with a sensed audio context of the wearer during the wearer activity, analyzing the audio context data, identifying the wearer activity based upon the analyses, and displaying the identity of the activity.

DESCRIPTION

Figure 1:
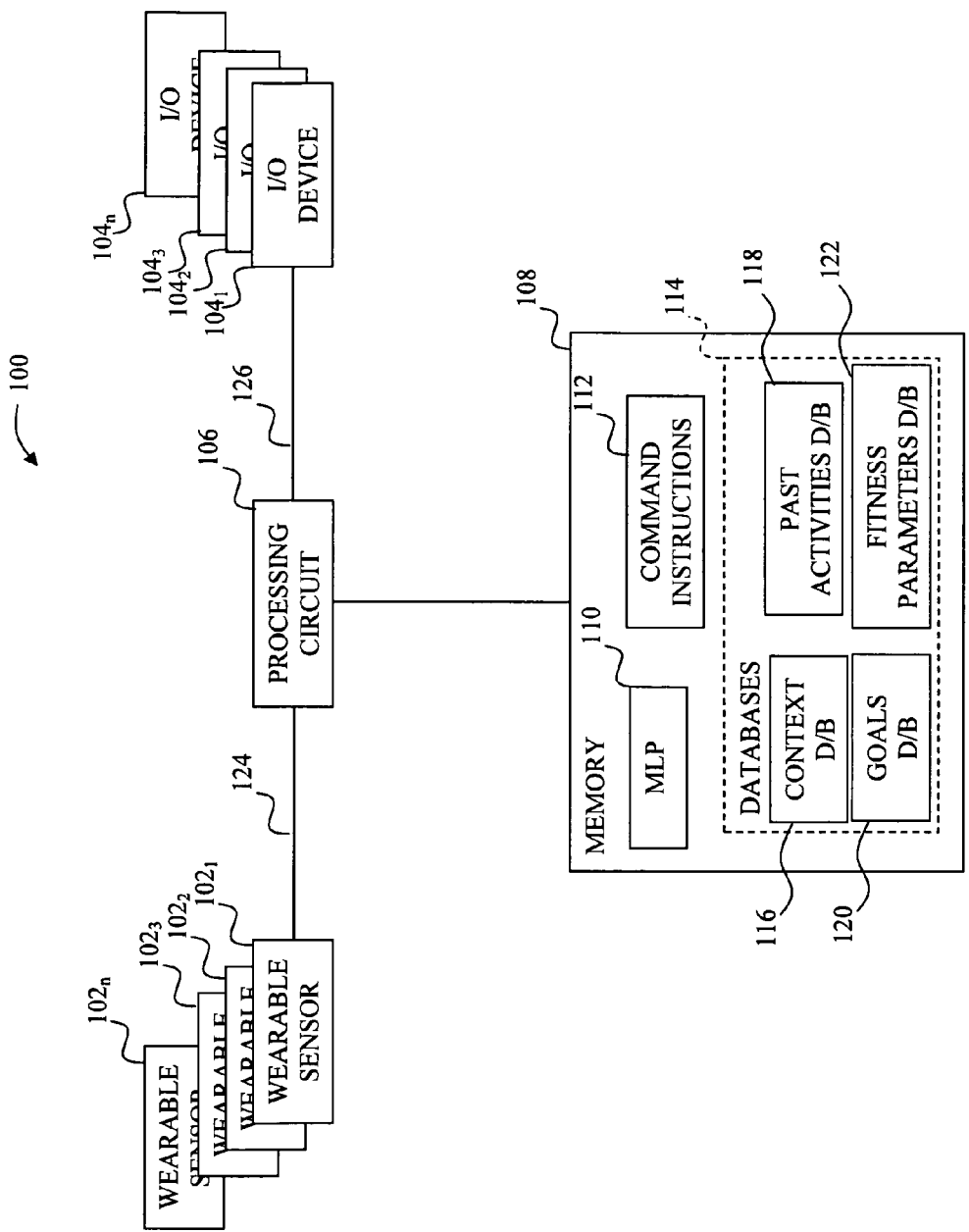
FIG. 1 depicts a block diagram of a physical activity monitoring network including wearable sensor devices in accordance with principles of the present invention.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring to FIG. 1, there is depicted a representation of a physical activity monitoring network generally designated 100. The network 100 includes a plurality of wearable sensors $102_x$, input/output (I/O) devices $104_x$, a processing circuit 106 and a memory 108. In one embodiment, a wearable sensor $102_x$, a processing circuit 106, and a memory 108 are provided in a single housing as a wearable unit.

The I/O devices $104_x$ may include a user interface, graphical user interface, keyboards, pointing devices, remote and/or local communication links, displays, and other devices that allow externally generated information to be provided to the processing circuit 106, and that allow internal information of the processing circuit 106 to be communicated externally.

The processing circuit 106 may suitably be a general purpose computer processing circuit such as a microprocessor and its associated circuitry. The processing circuit 106 is operable to carry out the operations attributed to it herein.

Within the memory 108 is a multilayer perceptron (MLP) 110 and program instructions 112. The program instructions 112, which are described more fully below, are executable by the processing circuit 106 and/or any other components as appropriate.

The memory 108 also includes databases 114. The databases 114 include a context database 116, a past activities database 118, a goals database 120, and a fitness parameters database 122. In one embodiment, the databases are populated using object oriented modeling. The use of object oriented modeling allows for a rich description of the relationship between various objects.

A communications network 124 provides communications between the processing circuit 106 and the wearable sensors $102_x$ while a communications network 126 provides communications between the processing circuit 106 and the I/O devices $104_x$. In alternative embodiments, some or all of the communications network 124 and the communications network 126 may include shared components.

In the embodiment described herein, the communications network 124 is a wireless communication scheme implemented as a wireless area network. A wireless communication scheme identifies the specific protocols and RF frequency plan employed in wireless communications between sets of wireless devices. To this end, the processing circuit 106 employs a packet-hopping wireless protocol to effect communication by and among the processing circuit 106 and the wearable sensors $102_x$.

Figure 2:
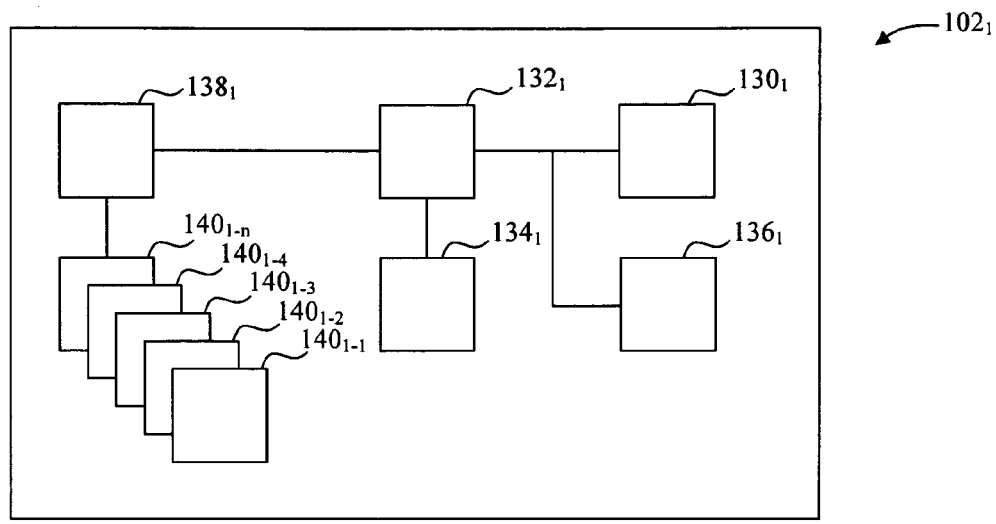
FIG. 2 depicts a schematic of a wearable sensor of FIG. 1 including at least one communication circuit and at least one sensor suite.

Each of the wearable sensors $102_x$ in this embodiment are identical and are described in more detail with reference to the wearable sensor $102_1$ shown in FIG. 2. The sensor $102_1$ includes a network interface $130_1$, a processor $132_1$, a non-volatile memory $134_1$, a micro-electrical mechanical system (MEMS) local RF communication interface $136_1$, a signal processing circuit $138_1$, and sensor suites $140_{1-x}$.

The network interface $130_1$ is a communication circuit that effectuates communication with one or more components of the communications network 124. To allow for wireless communication with the other components of the communications network 124, the network interface $130_1$ is preferably a radio frequency (RF) modem configured to communicate using a wireless area network communication scheme such as Bluetooth RF modem, or some other type of short range (about 30-100 feet) RF communication modem. Thus, each of the sensors $102_x$ may communicate with components such as other communication subsystems and the processing circuit 106.

The network interface $130_1$ is further operable to, either alone or in conjunction with the processor $132_1$, interpret messages in wireless communications received from external devices and determine whether the messages should be retransmitted to another external device as discussed below, or processed by the processor $132_1$. Preferably, the network interface $130_1$ employs a packet-hopping protocol to reduce the overall transmission power required. In packet-hopping, each message may be transmitted through multiple intermediate communication subsystem interfaces before it reaches its destination as is known in the relevant art.

The processor $132_1$ is a processing circuit operable to control the general operation of the sensor $102_1$. In addition, the processor $132_1$ may implement control functions and information gathering functions used to maintain the databases 114.

The programmable non-volatile memory $134_1$, which may be embodied as a flash programmable EEPROM, stores configuration information for the sensor suites $140_{1-x}$. The programmable non-volatile memory $134_1$ includes an "address" or "ID" of the wearable sensor $102_1$ that is appended to any communications generated by the wearable sensor $102_1$. The memory $134_1$ further includes set-up configuration information related to the system communication parameters employed by the processor $132_1$ to transmit information to other devices.

The MEMS local RF communication circuit $136_1$ may suitably include a Bluetooth RF modem, or some other type of short range (about 30-100 feet) RF communication modem. The use of a MEMS-based RF communication circuit allows for reduced power consumption, thereby enabling the wearable sensor $102_1$ to be battery operated, if desired. The life of the wearable sensor $102_1$ may be extended using power management approaches. Additionally, the battery may be augmented or even replaced by incorporating structure within the MEMS module to use or convert energy in the form of vibrations or ambient light. In some embodiments, a single circuit functions as both a network interface and a local RF communication circuit.

The local RF communication circuit $136_1$ may be self-configuring and self-commissioning. Accordingly, when the wearable sensors $102_x$ are placed within communication range of each other, they will form a piconet as is known in the relevant art. In the case that a wearable sensor $102_x$ is placed within range of an existent piconet, the wearable sensor $102_x$ will join the existent piconet.

Figure 3:
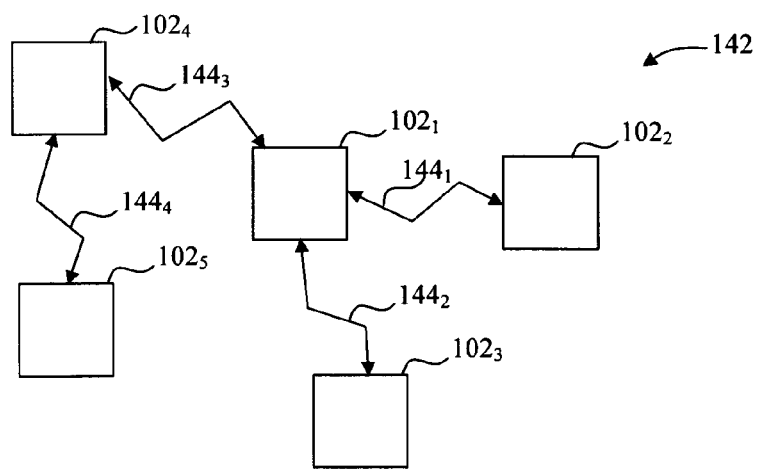
FIG. 3 depicts the wearable sensors of FIG. 1 connected into a piconet.

Accordingly, the wearable sensors $102_x$ are formed into one or more communication subsystems 142 as shown in FIG. 3. The wearable sensors $102_x$ within the communication subsystem 142 include a hub wearable sensor $102_1$, and slave wearable sensor $102_2$, $102_3$, and $102_4$. Additionally, a slave transmitter $102_5$ is within the communication subsystem 142 as a slave to the slave transmitter $102_4$. The hub sensor $102_1$ establishes a direct connection with the processing circuit 106 over the network 124. The slave wearable sensor 102$_2$, 102$_3$, 102$_4$, and 102$_5$ communicate with the processing circuit 106 through the hub sensor 102$_1$. It will be appreciated that a particular communication subsystem 142 may contain more or fewer wearable sensors 102$_x$ than the wearable sensors 102$_x$ shown in FIG. 3.

Thus, each of the communication circuits 136$_x$ in the wearable sensors 102$_1$, 102$_2$, 102$_3$, and 102$_4$ is used to link with the communication circuits 136$x$ in the other wearable sensors 102$_x$ to establish piconet links 144$_{1-3}$ (see FIG. 3). The communication circuits 136$_x$ of the slave wearable sensors 102$_4$ and 102$_5$ also establish a piconet link 144$_4$.

Returning to FIG. 2, the signal processing circuit 138$_1$ includes circuitry that interfaces with the sensor suites 140$_{1-x}$, converts analog sensor signals to digital signals, and provides the digital signals to the processor 132$_1$. In general, the processor 132$_1$ receives digital sensor information from the signal processing circuit 138$_1$, and from other sensors 102$_x$, and provides the information to the communication circuit 124.

The sensor suites 140$_{1-x}$ include a sensor suite 140$_{1-1}$ which in this embodiment is a 3-axis gyroscope sensor suite which provides information as to the orientation of the wearable sensor 102$_1$. Other sensors which may be incorporated into the sensor suites 140$_{1-x}$ include a calorimeter, a pulse sensor, a blood oxygen content sensor, a GPS sensor, and a temperature sensor. One or more of the sensor suites 140$_{1-x}$ may include MEMS technology.

Figure 4:
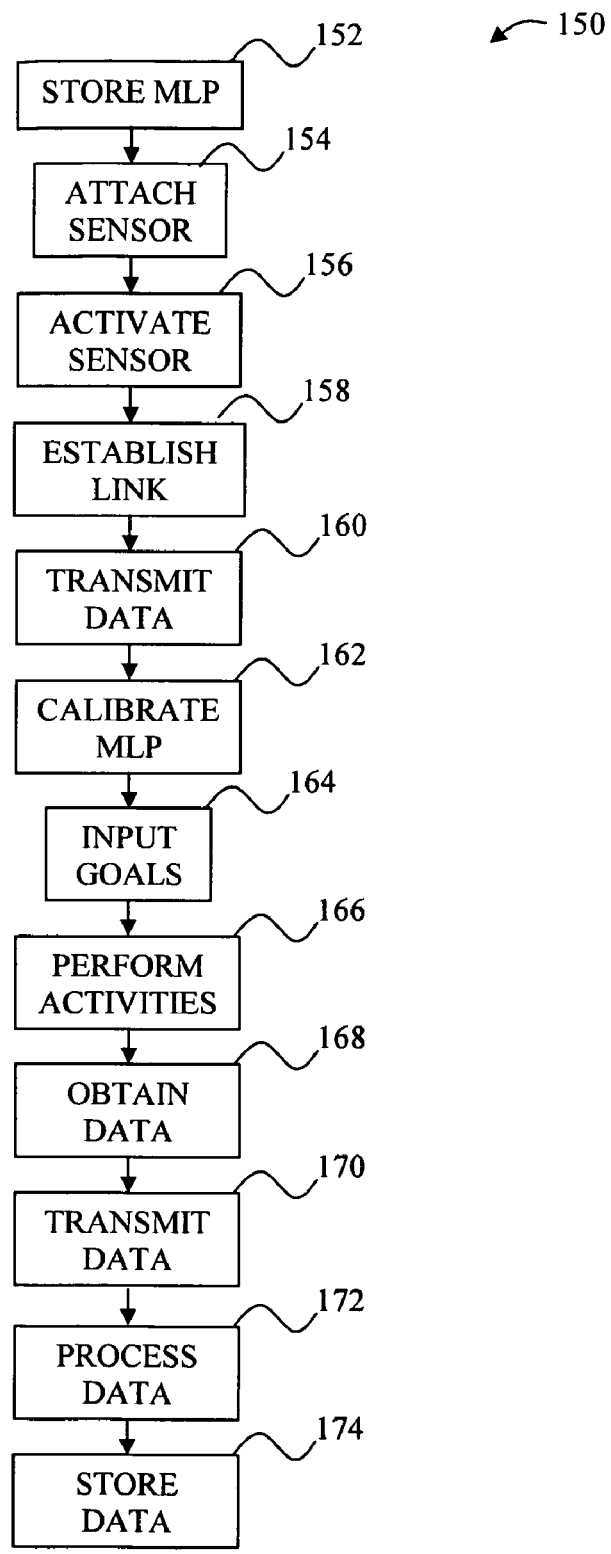
FIG. 4 depicts a process that may be controlled by the processor of FIG. 1 for obtaining physical activity monitoring data from the wearable sensors of FIG. 1.

Referring to FIG. 4, there is depicted a flowchart, generally designated 150, setting forth an exemplary manner of operation of the network 100. Initially, the MLP 110 may be stored within the memory 108 (block 152). The MLP 110 in one embodiment includes 30 hidden layer neurons and 1 output neuron. The activation function for the hidden layer and output layer neurons are hyperbolic tangent sigmoid and log sigmoid, respectively. Next, a wearable sensor 102$_x$ is placed on a subject such as an individual (block 154). The wearable sensor 102$_x$ is then activated (block 156). Upon activation of the sensor 102$_x$, the processor 132 initiates' data capture subroutines. Additionally, the wearable sensor 102$_x$ establishes the communications link 124 with the processing circuit 106 (block 158). Alternatively, the wearable sensor 102$_x$ may join a piconet or other communication system in communication with the processing circuit 106.

Initial output from the sensor suites 140$_x$ is passed through the signal processing circuit 138$_x$ to the processor 132$_x$. The initial sensor data is then transmitted to the processing circuit 106 over the link 124 (block 160). The initial sensor data is used by the processing circuit 106 to calibrate the MLP 110 (block 162). Calibration of the MLP 110 provides the MLP 110 with an initial state for the subject wearing the sensor 102$_x$. For example, the output of the sensor suite 140$_{1-1}$ is used to establish y-axis and z-axis values for the wearer of the sensor 102$_x$, in a known position such as standing or prostate.

The goals database 120 (block 164) is then populated. The data used to populate the goals database 120 may be input from one or more of the I/O devices 104$_x$. Alternatively, the sensor 102$_x$ may be configured with a user interface, allowing the wearer of the sensor 102$_x$ to input goals data.

The wearer then proceeds to perform various physical activities (block 166). As the activities are performed, data is obtained from the sensor suites 140$_x$ (block 168). The sensor data is passed through the signal processing circuit 138$_x$ to the processor 132$_x$. The sensor data is then transmitted to the processing circuit 106 over the link 124 (block 170). The sensor data is processed by the processing circuit 106 (block 172) and stored in the databases 114 (block 174). By way of example, heart rate, respiration rate, temperature, blood oxygen content, and other physical parameters may be stored in the fitness parameters database 122.

The foregoing actions may be performed in different orders. By way of example, goals may be stored prior to attaching a sensor 102$_x$ to a subject. Additionally, the various actions may be performed by different components of the network 100. By way of example, in one embodiment, all or portions of the memory 108 may be provided in the sensor 102$_x$. In such an embodiment, the output of the MLP 110 may be transmitted to a remote location such as a server remote from the sensor for storage.

Figure 5:
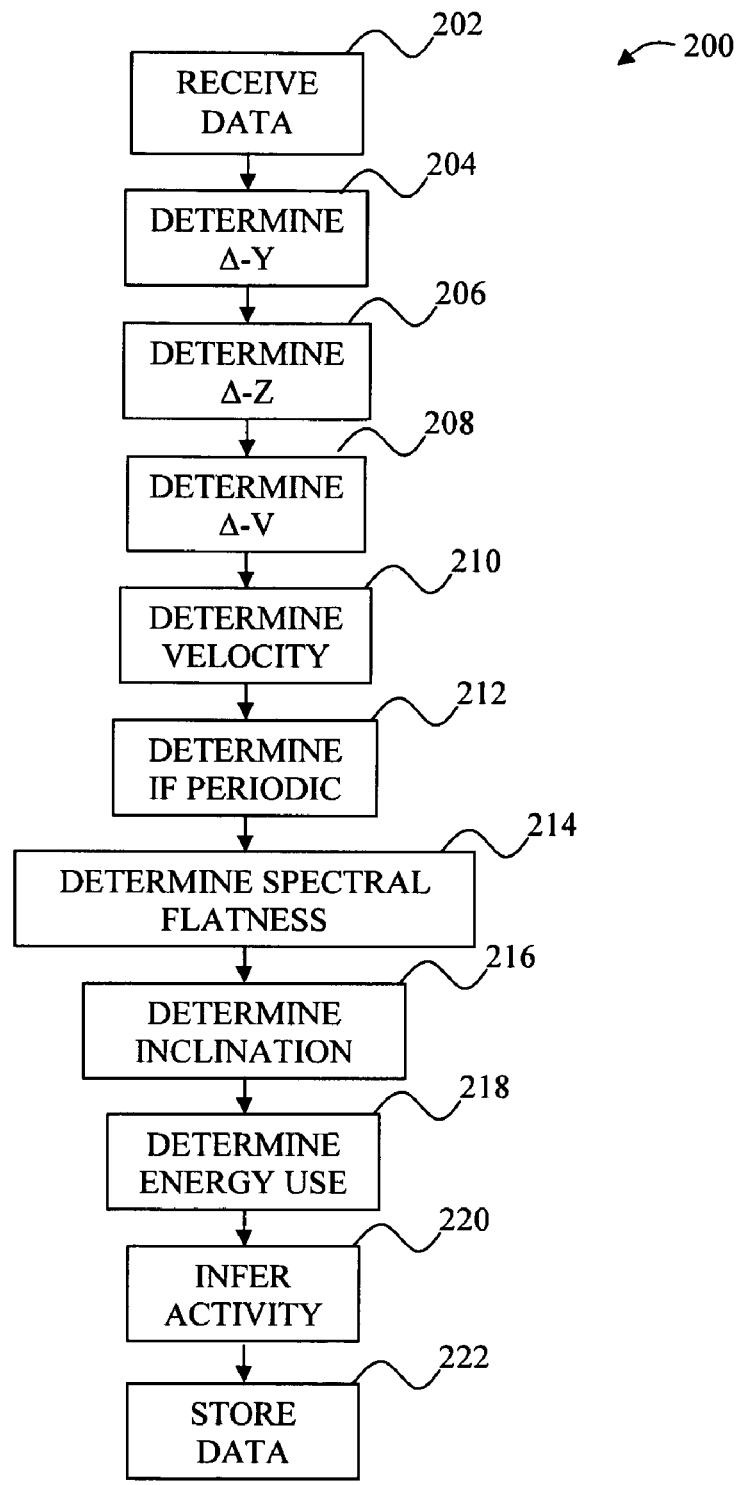
FIG. 5 depicts a process of analyzing data from a wearable sensor of FIG. 1 to generate an inference as to the activity of a subject wearing a wearable sensor using a multilayer perceptron.

The MLP 110 in one embodiment is configured to identify the activity in which the wearer of the sensor 102$_x$ is engaged. Accordingly, the MLP 110 is configured to perform the procedure 200 of FIG. 5. The processing circuit 106 receives a frame of data from the sensor suite 140$_{1-1}$ (block 202). One frame of data in one embodiment is based upon a ten second sample. Based upon the initial calibration data (block 162 of FIG. 4) and the most recently received frame data, the change in the orientation of the wearer in the y-axis is determined (block 204). Similarly, based upon the initial calibration data (block 162 of FIG. 4) and the most recently received frame data, the change in the orientation of the wearer in the z-axis is determined (block 206).

The frame data from the sensor suite 140$_{1-1}$ is also used to obtain a three dimensional vector indicative of the acceleration of the wearer (block 208) and to determine the three dimensional velocity of the wearer (block 210). Once the acceleration in the z-axis is obtained, the MLP 110 determines whether or not the acceleration in the z-axis is periodic (block 212). Periodicity is determined by analyzing several frames of frame data using an autocorrelation sequence formed from the z-axis acceleration.

The spectral flatness measure of the acceleration in all three axes is then determined (block 214). The spectral flatness measure is defined as the ratio of geometric mean to arithmetic mean of the power spectral density coefficients.

The data from the sensor suite 140$_{1-1}$ is further used to determine the relative inclination of the wearer (block 216) and data indicative of the energy use of the wearer is also obtained from the frame data and the energy expenditure is determined (block 218). Energy usage may be determined, for example, from data obtained by a sensor suite 140$_{1-x}$ configured as a thermometer or calorimeter.

Thus, the MLP 110 is configured to receive eight static features from a current input frame and eight delta features that capture the difference between the features in the current frame and those in a previous frame. Based upon the foregoing determinations, the MLP 110 infers an activity of the wearer for the time frame associated with the frame data. By way of example, relative inclination, periodicity and spectral flatness help distinguish between sitting, standing and lying-down. Additionally, energy expenditure, velocity, spectral flatness, and periodicity help distinguish between dynamic activities (e.g., walking) and static activities (e.g., standing). The activity determined by the MLP 110 is then stored, with a date/time stamp, in the past activities database 118 (block 222).

While the MLP 110 is controlled to make a determination as to the nature of the activity of the wearer, date/time stamped data is also being provided to the context database 116. For example, in embodiments incorporating a GPS sensor in a sensor suite 140$_{1-x}$, GPS data may be obtained at a given periodicity, such as once every thirty seconds, transmitted to the processing circuit 106 and stored in the context database 116. Additionally, data identifying the other transmitters in the piconet 142 is stored in the context database. Of course, transmitters within the piconet 142 need not be associated with a wearable sensor $102_x$. For example, a cellular telephone or PDA without any sensors may still emit a signal that can be detected by the sensor $102_x$.

The data within the memory 108 may be used in various applications either in real time, for example, by transmitting data over the communications link 124 to the sensor $102_x$, or at another time selected by the wearer or other authorized individual by access through an I/O device $104_x$. The applications include activity monitoring, activity recording, activity goal setting, and activity reviewing.

Figure 6:
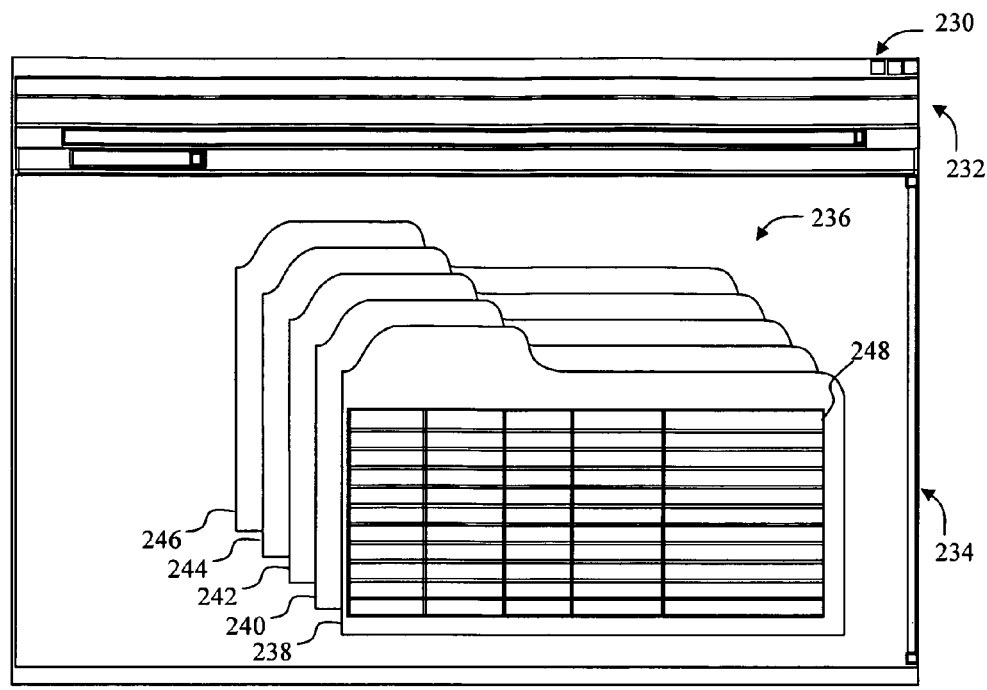
FIG. 6 depicts a screen that may be transmitted over a communications link such as the Internet and used to display obtained physical activity monitoring data from the wearable sensors of FIG. 1.

A screen which may be used to provide activity monitoring data from the memory 108, such as when the data is accessed by an I/O device $104_x$ connected to the memory 108 by an internet connection, is depicted in FIG. 6. The screen 230 includes a navigation portion 232 and a data portion 234. A number of folders 236 are rendered within the data portion 234. The folders 236 include a summary folder 238, an activity monitoring folder 240, an activity recording folder 242, an activity goal setting folder 244, and an activity reviewing folder 246. The summary folder 238 includes a chart 248. Data that may be rendered on the chart 248 include identification of the individual or subject associated with the sensor $102_x$, summary fitness data, and other desired data.

Figure 7:
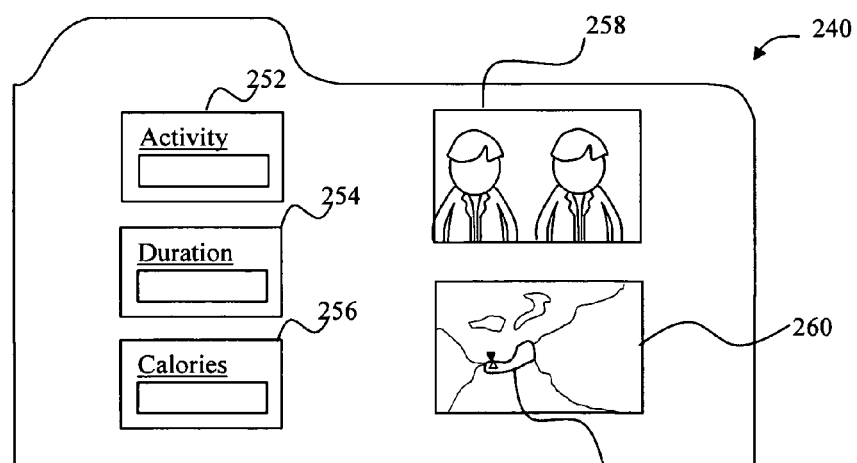
FIG. 7 depicts the contents of an exemplary activity information folder rendered within the screen of FIG. 6.

By selecting the activity monitoring folder 240, the folder 240 is moved to the forefront of the screen 230. When in the forefront, a viewer observes the folder 240 as depicted in FIG. 7. The activity monitoring folder 240 displays data related to the current activity of the subject. In this embodiment, the activity monitoring folder 240 displays data fields 252, 254, and 256 which are used to display the type of activity, the duration that the activity has been engaged in, and the calories used during the activity, respectively. The data fields presented for different activities may be modified. For example, if the subject is sleeping, the data fields may indicate respiration rate, heart beat rate, and blood oxygen content.

The activity monitoring folder 240 further identifies other subjects or individuals in proximity to the monitored subject in a context window 258. The context window 258 may identify specific individuals if known. A map 260 is also shown. Data for rendering the map 260 may be obtained, for example, from a GPS sensor in the sensor suite $140_x$ or from data obtained from a relay station. For embodiments including a GPS sensor in the sensor suite $140_x$, or other sensor for obtaining detailed location data, the route 262 of the subject over the course of the monitored activity may also be displayed on the map 260.

Figure 8:
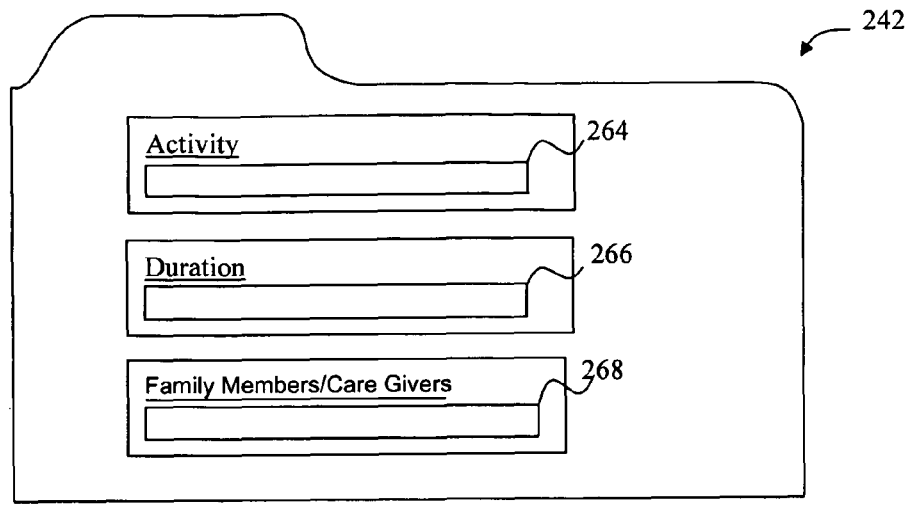
FIG. 8 depicts the contents of an exemplary record activity folder rendered within the screen of FIG. 6.

By selecting the activity recording folder 242 from the screen 230 of FIG. 6, the folder 242 is moved to the forefront of the screen 230. When in the forefront, a viewer observes the folder 242 as depicted in FIG. 8. In this embodiment, the activity recording folder 242 displays editable data fields 264, 266, and 268. The editable data fields 264, 266, and 268 allow a user to add or modify information related to a recorded activity. For example, unidentified workout partners may be identified to the network 100 by editing the field 268. This data may be used to modify the context database 116 so that the network 100 recognizes the workout partner in the future. For example, an individual's identity may be associated with a particular cell phone beacon that was detected with the wearable sensor $102_x$. The activity recording folder 242 may include additional editable fields.

Figure 9:
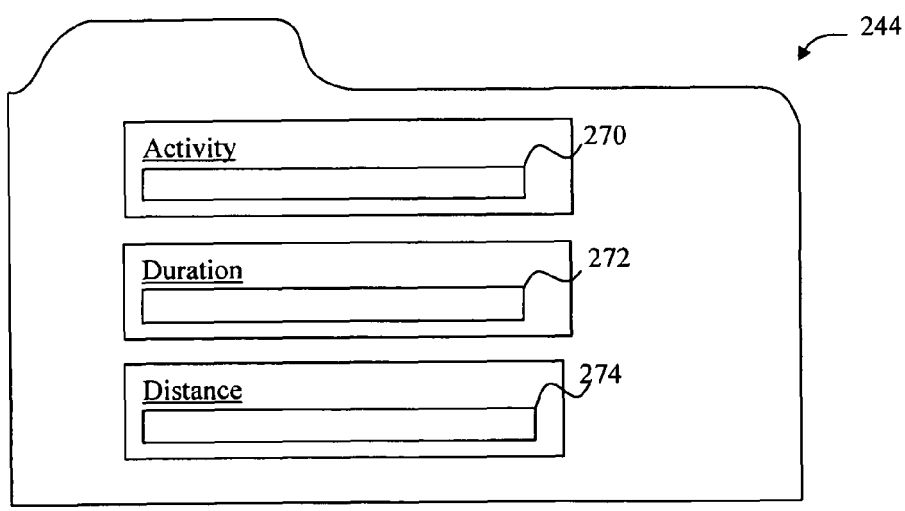
FIG. 9 depicts the contents of an exemplary goals folder rendered within the screen of FIG. 6.

By selecting the activity goal setting folder 244 from the screen 230 of FIG. 6, the folder 244 is moved to the forefront of the screen 230. When in the forefront, a viewer observes the folder 244 as depicted in FIG. 9. In this embodiment, the activity goal setting folder 244 displays editable data fields 270, 272, and 274. The editable data fields 270, 272, and 274 allow a user to record goals for future activity. For example, a goal of "Walking" may be identified in the field 270 and a duration of 90 minutes may be stored in the field 272. Additionally, a distance goal of, for example, 3 miles may be edited into field 274. The activity goal setting folder 244 may include additional editable fields such as average speed, etc.

Figure 10:
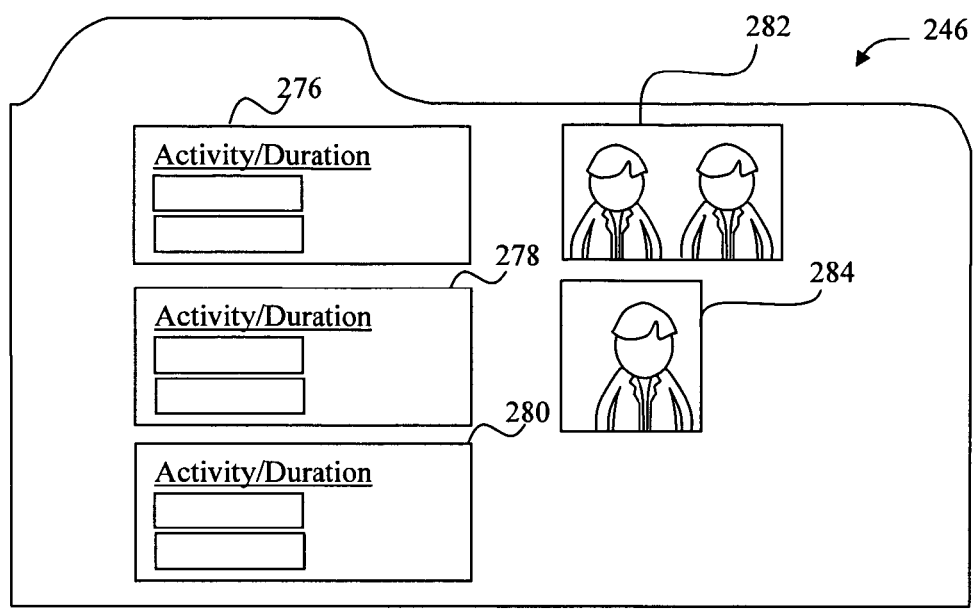
FIG. 10 depicts the contents of an exemplary activity review folder rendered within the screen of FIG. 6.

By selecting the activity reviewing folder 246 from the screen 230 of FIG. 6, the folder 246 is moved to the forefront of the screen 230. When in the forefront, a viewer observes the folder 246 as depicted in FIG. 10. In this embodiment, the activity reviewing folder 246 displays activity data fields 276, 278, and 280. The activity data fields 276, 278, and 280 allow a user to review activities which were conducted over a user defined time frame. Additional information may also be displayed. For example, context data fields 282 and 284 identify other individuals that were present during the activity associated with the data in the activity data fields 276 and 278, respectively.

Figure 11:
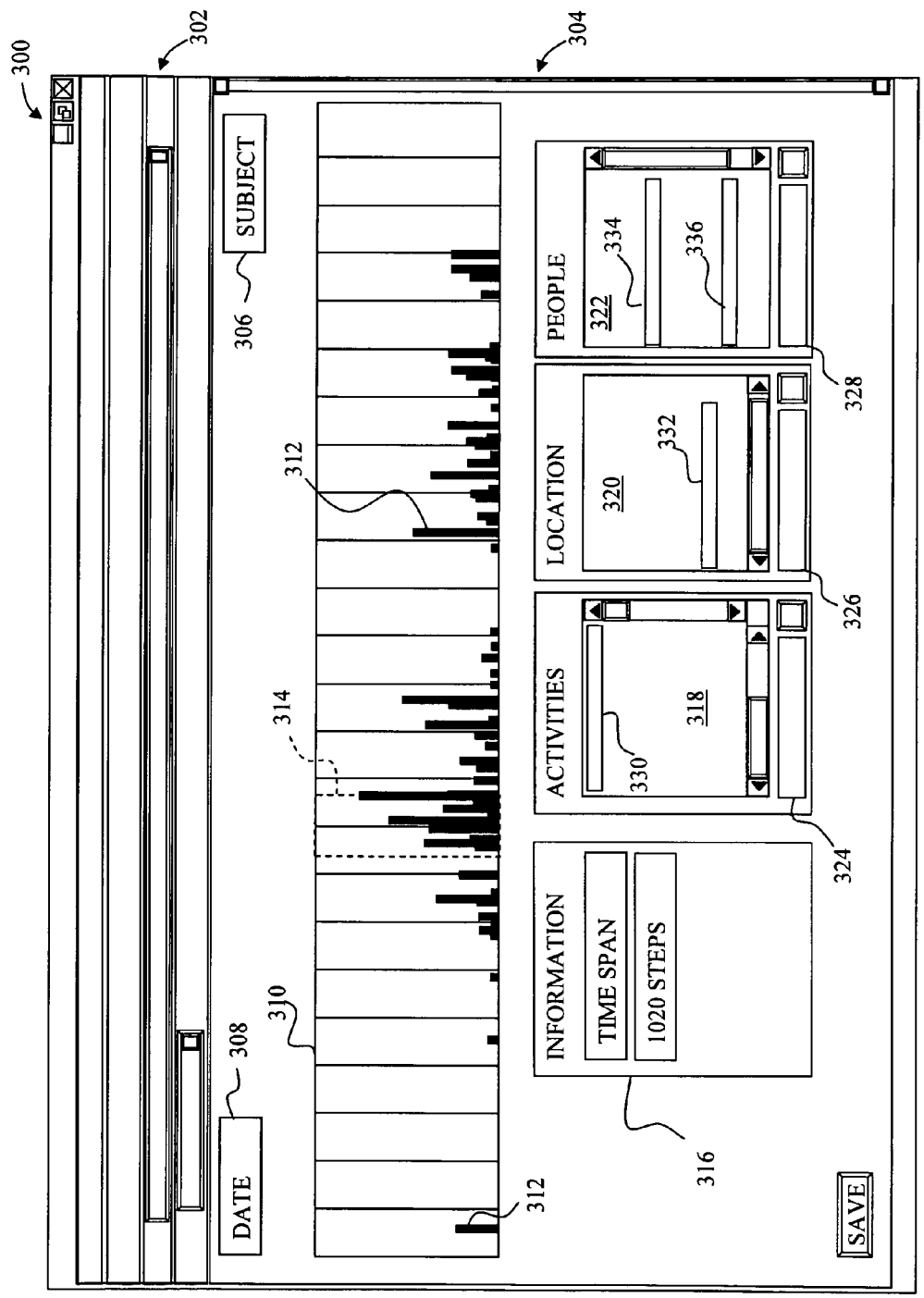
FIG. 11 depicts an alternative screen that may be accessed by a user to review activity of a subject over a twenty-four hour period including a graphic display of energy used, a summary of activity within a focus window, identification of activities within the focus window, the location at which the activities in the focus window were performed, and others accompanying the subject during performance of the activity.

A variety of different screens may be used to display data obtained from the memory 108. Additionally, the data selected for a particular screen, along with the manner in which the data is displayed, may be customized for different applications. For example, the screen 300 depicted in FIG. 11 may be used to provide an easily navigable interface for reviewing activities over a twenty-four hour window.

The screen 300 includes a navigation portion 302 and a data portion 304. The data portion 304 includes an identification field 306 for identifying the subject and a data field 308 which displays the date associated with the data in the data portion 304.

A daily activity chart 310 within the data portion 304 shows the amount of calories expended by the subject. To this end, bar graphs 312 indicate caloric expenditure over the twenty-four hour period depicted in the chart 310. The data for the bar graphs 312 may be obtained, for example, from the past activities database 118.

A focus window 314 is controlled by a user to enclose a user variable window of activity. In response, the underlying application accesses the databases 114 and displays data associated with the focus window 314 in an information field 316, an activities field 318, a location field 320, and a people field 322.

The information field 316 displays general data about the focus window 314. Such data may include the time span selected by the user, the amount of calories expended during the selected time span, the number of steps taken by the subject during the selected time span, maximum speed of the subject during the selected time span, average speed of the subject during the selected time span, etc.

The activities field 318 displays each identifiable activity within the focus window 314. The activity may be specifically identified or generally identified. For example, the network 100 may initially only be configured to distinguish activities based upon, for example, changes in velocity, changes in respiration, changes in heart rate, etc. Thus, the activity identification may be "activity 1," "walking," or "running".

The activities field 318 includes, however, an editable field 324. The field 324 may be used to edit the identified activity with additional descriptive language. Thus, the general identification may be further specified as "loading boxes on a truck", "cutting grass", "raking leaves", etc. Moreover, the network 100 may be configured to "learn" so as to infer a more specific identification of future activities.

The location field 320 displays context data in the form of each identifiable location at which the activities within the focus window 314 were conducted. The location may be specifically identified or generally identified. For example, the network 100 may initially only be configured to distinguish location based upon a determined change in location. The location field 320 includes, however, an editable field 326. The field 326 may be used to edit the identified location with additional descriptive language. Thus, the general identification of a "location 1" may be further specified as "gym", "office" or "jogging route 1".

The people field 322 displays context data in the form of each identifiable individual or subject present during the activities within the focus window 314. The people may be specifically identified or generally identified. For example, the MLP 110 may initially only be configured to distinguish different individuals based upon a different cell phone beacons. The people field 322 includes, however, an editable field 328. The field 328 may be used to edit the identified individual with additional descriptive language. Thus, the general identification of an "individual 1" may be further specified as "Joe", "Anastasia" or "co-worker".

Various functionalities may be incorporated into the screen 300 in addition to the functions set forth above so as to provide increased insight into the habits of a subject. By way of example, in response to selecting an activity within the activity field 318, the context data for the selected activity may be highlighted. Thus, by highlighting the area 330 in the activities field 318, a location 332 and individuals 334 and 336 are highlighted.

Figure 12:
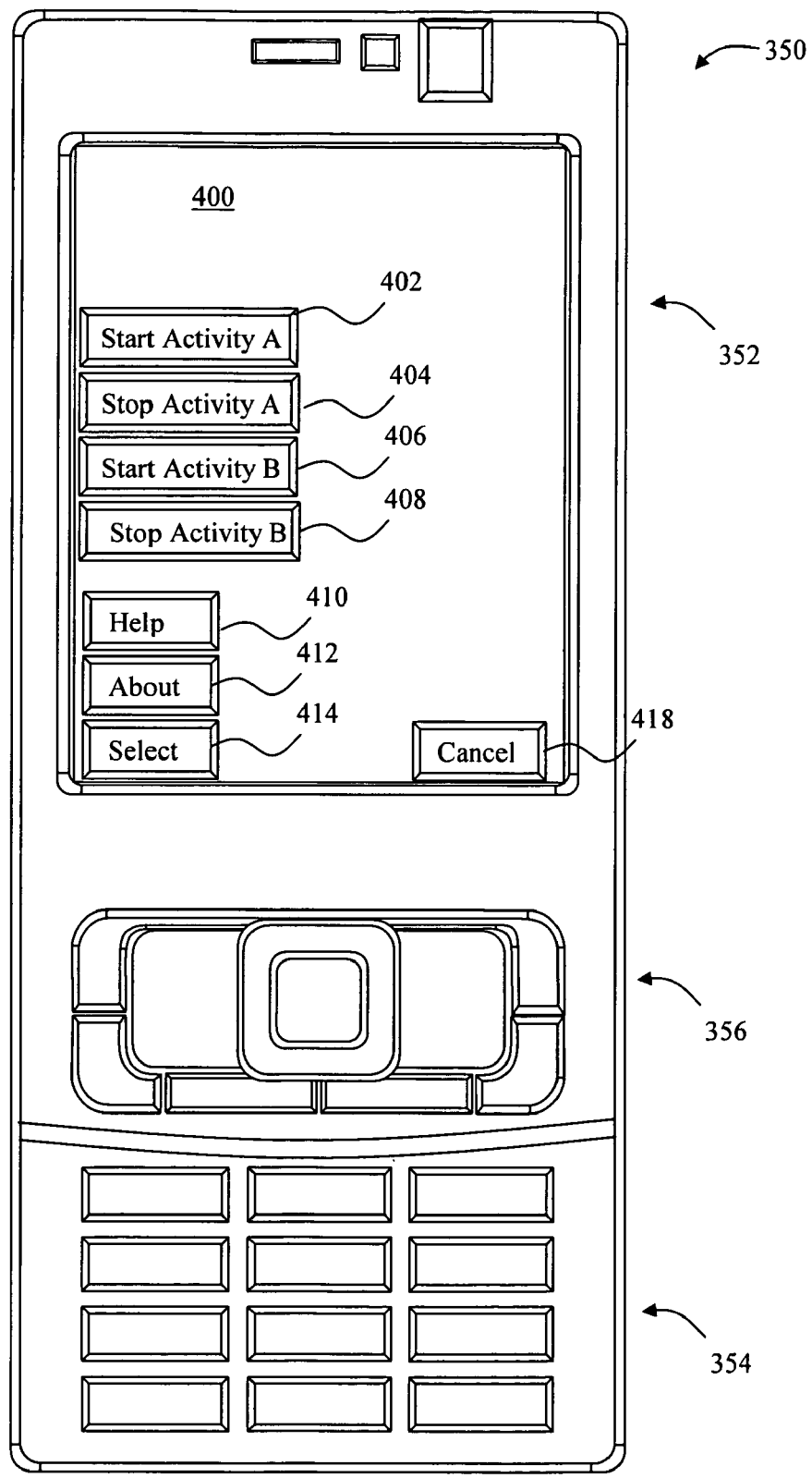
FIG. 12 depicts an alternative wearable sensor device that may be used as a telephone so as to link with the system of FIG. 1 through either different types of communication systems.
Figure 13:
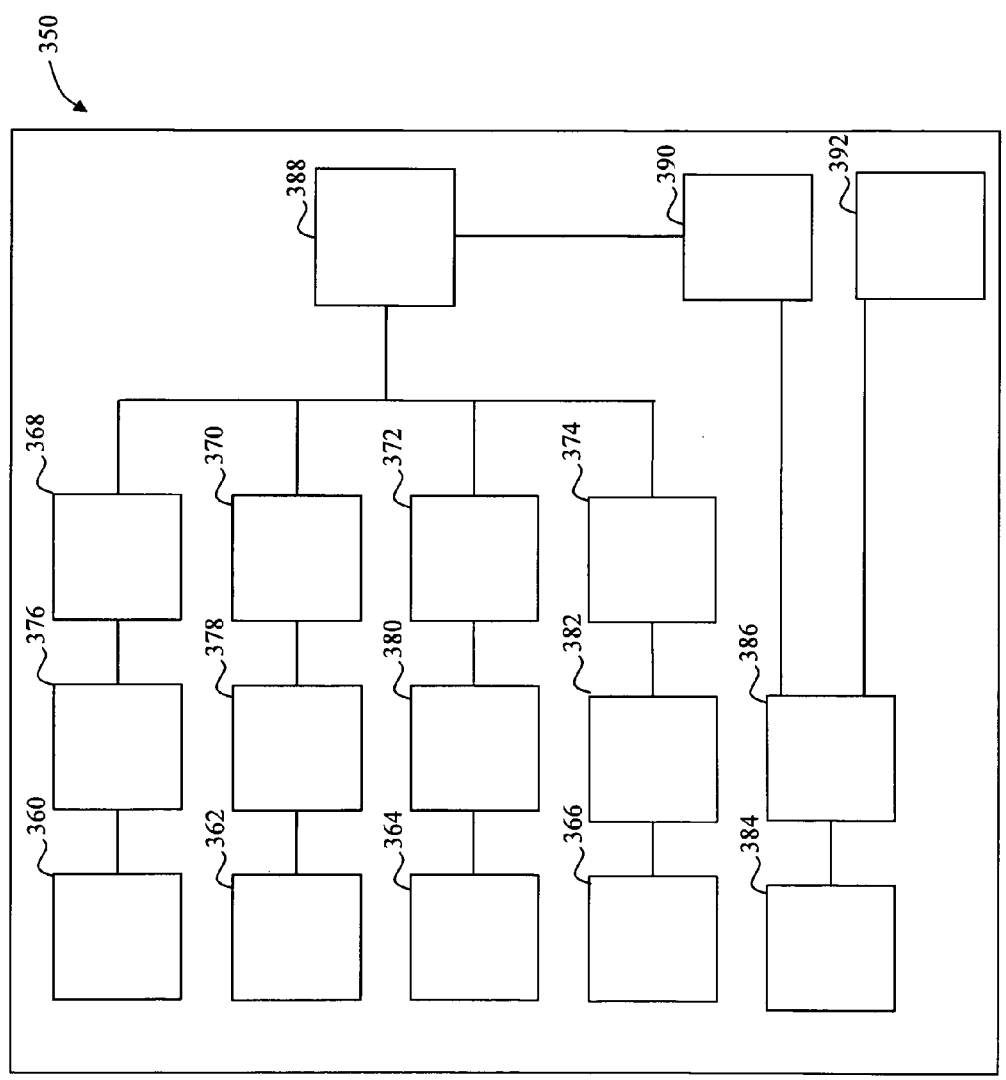
FIG. 13 depicts a schematic of the wearable sensor of FIG. 1 including at least one communication circuit and at least one sensor suite.

Additional functionalities may also be incorporated into a wearable sensor device. FIG. 12 depicts another embodiment of a wearable sensor device 350 which provides additional functionalities. The wearable sensor device 350 is a Smartphone which includes a screen portion 352, a keypad 354 and a mouse 356. A schematic of the architecture of the wearable sensor device 350 is depicted in FIG. 13.

The wearable sensor device 350 includes a microphone sensor 360, an accelerometer sensor 362, a GPS sensor 364, and a GSM sensor 366. Each of the sensors 360, 362, 364, and 366 is connected to a respective data collection client 368, 370, 372 and 374 through a respective operating system server 376, 378, 380, and 382. The wearable sensor device 350 further includes a flash memory reader 384 which is operably connected to an operating system server 386. Each of the operating system servers 376, 378, 380, 382, and 386 may suitably be a SYMBIAN operating system, commercially available from Nokia Corporation of Harrison, N.Y.

The sensor data collection clients 368, 370, 372, and 374 are configured to date/time stamp data received from the sensors 360, 362, 364, and 366 and are operably connected to an activity inference engine 388 which feeds a flash client 390. The flash client 390 feeds the operating system server 386 which provides output to a flash client 392.

The wearable sensor device 350 is configured to establish communications with the processing circuit 106 of FIG. 1 over the link 124. Accordingly, output from the activity inference engine 388 may transmitted to the processing circuit 106.

The activity inference engine 388 allows the wearable sensor device 350 to generate activity data and context data prior to transmission of sensor related data. To this end, the wearable sensor device 350 may access the processing circuit by establishing communications over the communications link 126 of FIG. 1 so as to store the activity data and context data generated by the wearable sensor device 350 in the databases 114 or to access the data in the databases 114.

Figure 14:
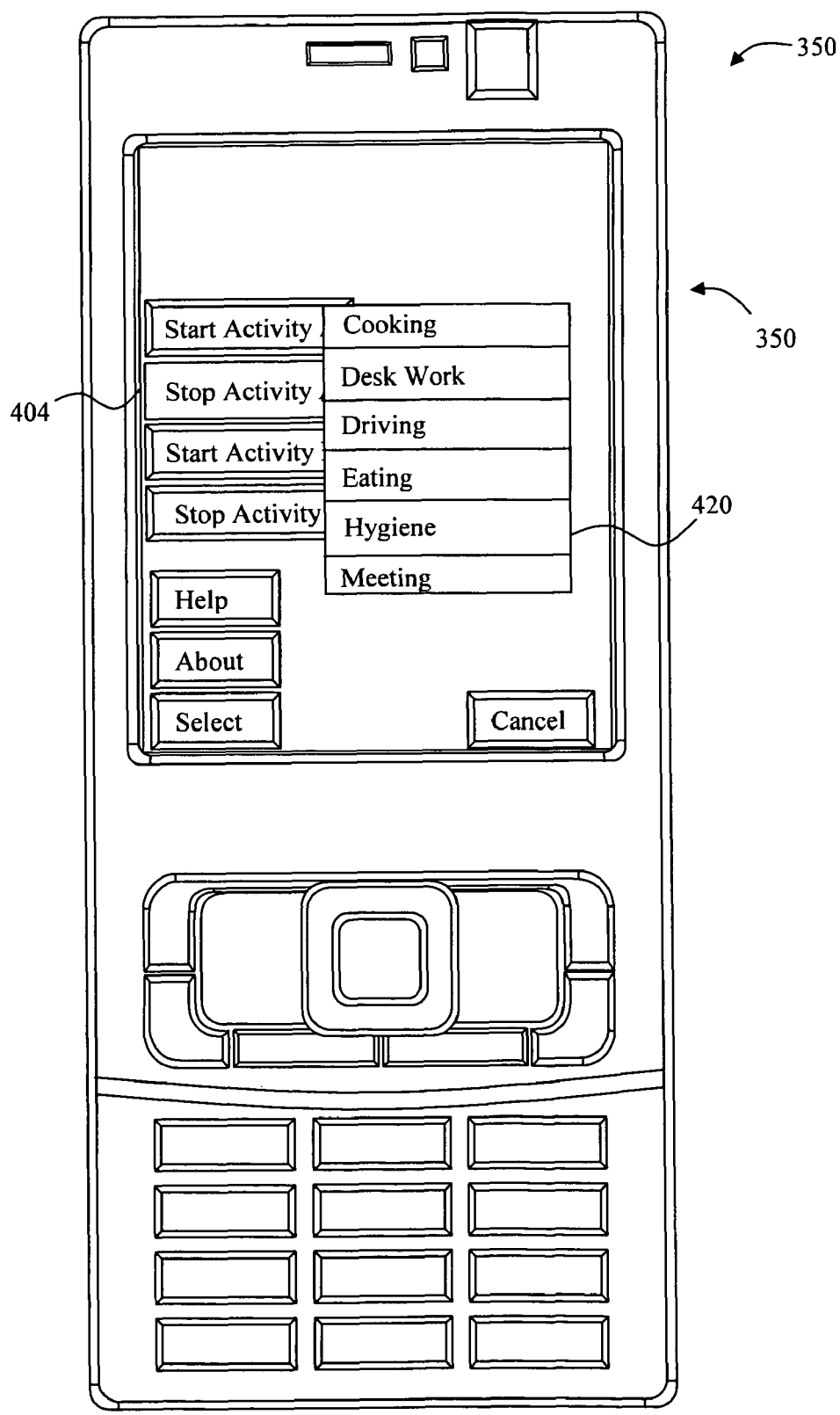
FIG. 14 depicts the wearable sensor of FIG. 12 being used to tag an activity to update the activity inference engine.

User input to the activity inference engine 388 is provided by an application which generates a screen 400 in the screen portion 352 as depicted in FIG. 12. The screen 400 includes tag buttons 402, 404, 406, and 408, help button 410, about button 412, select button 414, and cancel button 418. The tag buttons 402, 404, 406, and 408 may be activated by a user to provide real-time input to the activity inference engine 388. By way of example, by selecting the button 404, the pop-up window 420 of FIG. 14 is rendered.

The pop-up window 420 presents, in this example, a list of the activities in which the wearer has been engaged in. By selecting one of the presented activities, the wearer indicates to the activity inference engine 388 which activity the wearer is no longer engaged in. When a new activity is commenced, selection of the button 402 or 406 may result in a pop-up window 314 which lists past activities of the wearer. In the event the activity is a new activity, the wearer may be provided with an editable field to input a name for the new activity.

As noted above, the wearable sensor device 350 includes a microphone sensor 360 which provides input to the activity inference engine 388. Audio context data from the microphone sensor 360 may be utilized by the activity inference engine 388 differently from the manner in which the MLP 110 utilizes context data because the activity inference engine 388 provides functionality not provided by the MLP 110.

Specifically, while the MLP 110 provided general activity data, the activity inference engine 388 provides a more detailed description of the activity of the user. In other words, while the MLP 110 may discriminate between activities such as sitting and standing, the activity inference engine 388 provides an intelligent inference as to the particular activity undertaken while, for example, sitting. The activity inference engine 388, discussed in more detail below, thus distinguishes between sitting activities such as working at a computer, eating, watching television, and doing military press exercises.

Figure 15:
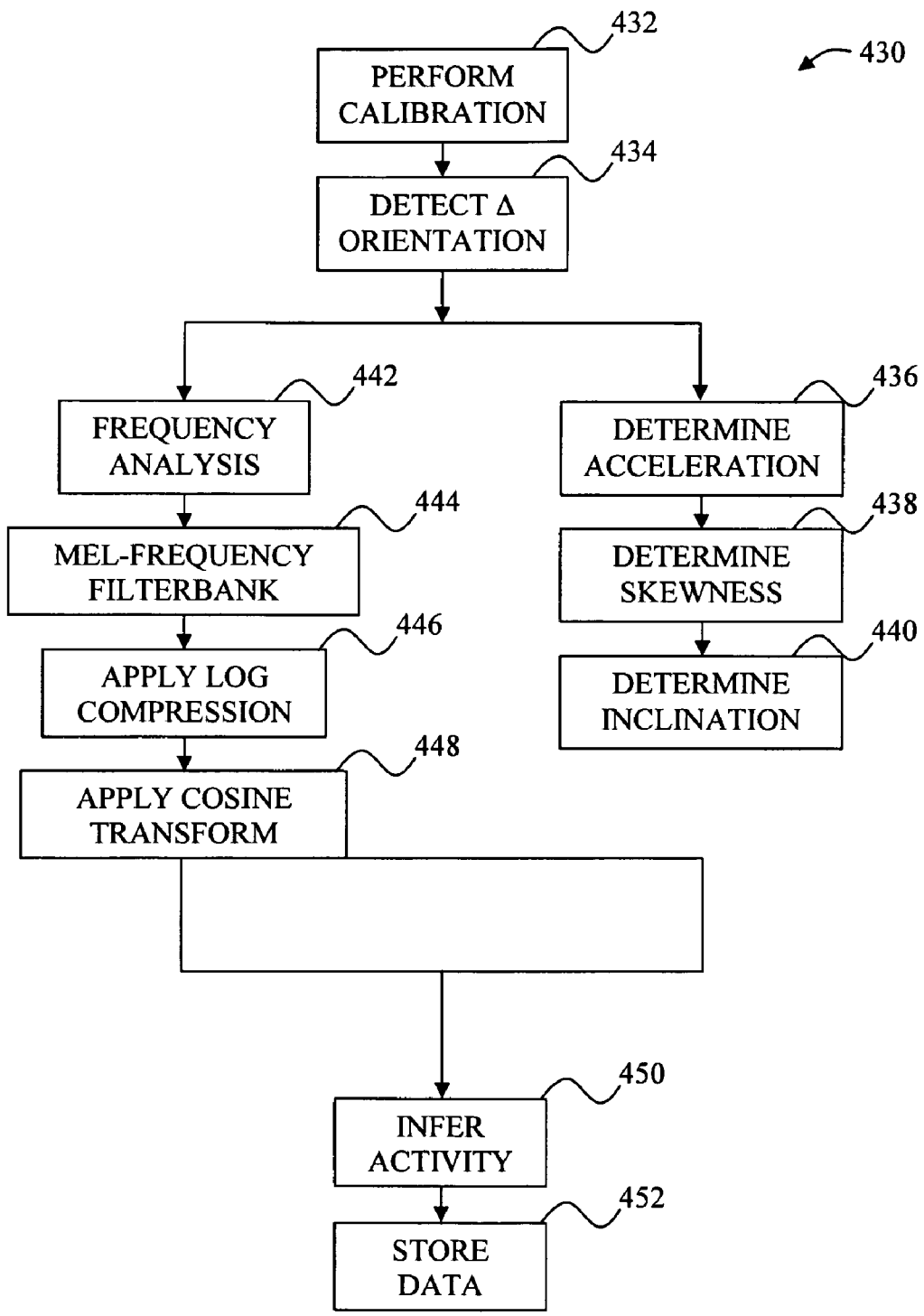
FIG. 15 depicts a process of analyzing data from the wearable sensor of FIG. 12 to generate an inference as to the activity of a subject wearing a wearable sensor using audio signals.

Accordingly, the activity inference engine 388 incorporates a hidden Markov Model (HMM) to model each activity sensed by the wearable sensor device 350. The input to the HMM includes various features derived from the sensed triaxial acceleration data in overlapping time. In one embodiment, the HMM follows a process 430 shown in FIG. 15

Initially, a calibration is performed (block 432). During the calibration, the wearer is presumed to be standing. Alternatively, another predefined activity may be used in the calibration. At block 434, a change is sensed in the body orientation of the user in the x-y-z planes with respect to the calibration phase.

Next, a 3-dimensional vector magnitude of acceleration is determined (block 436). The magnitude of the 3-dimensional acceleration is related to the energy expended in performing a particular physical activity such as walking. The skewness of the magnitude of the 3-dimensional acceleration is also computed (block 438). At block 440, the entropy of the acceleration in the z-axis is computed to provide insight as to the relative inclination of the wearer. Relative inclination assists in distinguishing activities that depend on whether a person is sitting (e.g., eating), standing (e.g., cooking), and lying-down (e.g., watching television).

The foregoing analysis provides energy expenditure, skewness, and entropy which may be used to distinguish between dynamic activities (e.g., aerobic activities) and static activities (e.g., desk work). To allow further distinction of the particular activity, analysis of the audio context data from the microphone sensor 360 is incorporated.

Processing of audio data is performed in parallel with the processing of the acceleration data. Initially, the audio signal is subjected to a frequency analysis for each frame of data (block 442). The data frame may have the same period as the data frames described above. The resulting speech spectra are then processed by a Mel-frequency filterbank (block 444). A log compression is then applied to the spectra (block 446) and the spectral coefficients are converted to cepstral coefficients (block 448).

The cepstral coefficients are then used to differentiate between classes of dynamic activities and between different classes of static activities. By way of example, while a "cooking" activity and a "hygiene" activity are both dynamic activities, the cepstral coefficients associated with the two activities are different. Similarly, while a "meeting" activity and a "driving" activity are both static activities, the cepstral coefficients associated with the two activities are different.

Accordingly, by analyzing the cepstral coefficients associated with an activity along with the other data discussed above with respect to blocks 434-440, an inference as to the activity may be generated (block 450). To assist in correlating the data from the various sensors, data obtained from the sensors may be date/time stamped by, for example, the respective sensor data collection clients 368, 370, 372, and 374. The various data and the inference are then stored (block 452). In one embodiment, the The network 100 thus provides not only insight as to a subject's activities such as standing, sitting, walking, fast walking and running, but can further be used to describe more specifically the activity conducted while standing, sitting, walking, fast walking and running by incorporating the wearable sensor device 350. These activities may be further inferred based upon features extracted from historical data. Additionally, by incorporation of a pre-learned classifier, such as a neural net-based classifier, the system can automatically learn new activity classifications.

The presentation of data, stored during the process 430, from the databases 114 in the manner described above with reference to FIGS. 6-11 provides improved accuracy in capturing action specific metrics such as energy expenditure for walking as opposed to that for fast walking or running. Moreover, increased granularity of detail is available to understand the difference in, e.g., energy expenditure, for different standing activities, different sitting activities, etc. By selectively displaying data stored within the databases 114, subject matter experts (SME) can use the captured historical data to identify factors implicated by past failures for the subject. This allows the SME to design innovative and effective ways of structuring future activities so as to increase the potential for achieving goals.

Additionally, while the data may be used retrospectively, the data may also be presented to a subject in real-time. Accordingly, an athlete may easily change his workout routine from walking to running and fast walking so as to maintain a desired rate of energy expenditure. Of course, the functionality of the network 100 can be expanded by provision of additional sensors located at multiple locations of the subject body. The network 100 may further be used to set goals and to monitor activities against the established goals. The data may be used to provide motivational feedback to the subject.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The invention claimed is:

1. A physical activity monitoring system comprising:
a communications network;
a wearable sensor device configured to generate physiologic data associated with a sensed physiologic condition of a wearer, and to generate audio context data associated with a sensed audio context of the wearer, and to form a communication link with the communications network;
a memory operably connected to the communications network and configured to receive and store the generated physiologic data and the generated audio context data;
a computer and a computer program executed by the computer, wherein the computer program comprises computer instructions for rendering activity data based on the stored physiologic data and the stored audio context data, wherein the stored audio context data is analyzed to distinguish between different activities, the computer operably connected to the memory and configured to obtain the stored physiologic data and the stored audio context data; and
a user interface operably connected to the computer for rendering the activity data.

2. The system of claim 1, wherein the wearable sensor device is configured to generate the audio context data based upon an audio signal received by the wearable sensor device.

3. The system of claim 2, wherein the received signal is generated by an activity of the wearer.

4. The system of claim 1, wherein:
the wearable sensor device is further configured to generate non-audio context data;
the memory is configured to store the non-audio context data; and
the computer program executed by the computer comprises computer instructions for associating the non-audio context data and the audio context data.

5. The system of claim 1, wherein the non-audio context data comprises:
the identification of an individual in the company of the wearer when the physiologic condition was sensed.

6. The system of claim 1, wherein the computer program comprises computer instructions for rendering:
activity information data;
activity recording data;
activity goal setting data; and
activity reviewing data.

7. The system of claim 1, further comprising a hidden Markov Model (HMM) stored within the memory and configured to:
determine a 3-dimensional vector magnitude of acceleration;
determine a magnitude of the 3-dimensional vector magnitude of acceleration; and
determine a skewness of the magnitude of the 3-dimensional vector magnitude of acceleration.

8. The system of claim 1, wherein the rendered activity data comprises an identity of an activity of the wearer, the activity associated with the generated audio context data.

9. The system of claim 1, wherein the rendered activity data is based upon at least one cepstral coefficient.

10. The system of claim 1, wherein the rendered activity data comprises an identification of a geographic location associated with the generated audio context data.

11. A method of displaying data associated with physical activities comprising:
   storing an activity inference engine;
   generating physiologic data associated with a sensed physiologic condition of the wearer during an activity;
   generating context data associated with a sensed audio context of the wearer during the activity;
   using the stored activity inference engine to determine the nature of the activity based upon the physiologic data and the context data, wherein the context data is analyzed to distinguish between different activities; and
   displaying first data associated with the sensed physiologic data and second data associated with the determined nature of the activity.

12. The method of claim 11, wherein using the stored activity inference engine comprises:
   determining a 3-dimensional vector magnitude of acceleration; and
   determining at least one cepstral coefficient.

13. The method of claim 11, wherein generating context data further comprises:
   generating context data associated with a received signal from a mobile device.

14. The method of claim 13, further comprising:
   displaying a name of an individual based upon the context data.

15. A method of monitoring physical activity comprising:
   attaching a sensor to a wearer;
   activating the sensor;
   generating physiologic data associated with a sensed physiologic condition of the wearer during a wearer activity;
   generating audio context data associated with a sensed audio context of the wearer during the wearer activity;
   analyzing the audio context data using a computer;
   identifying the wearer activity based upon the analyses; and
   displaying the identity of the activity.

16. The method of claim 15, further comprising:
   generating non-audio context data associated with a sensed non-audio context of the wearer during the wearer activity; and
   displaying the non-audio context data.

17. The method of claim 16, wherein displaying the non-audio context data comprises:
   displaying a name of a geographic location.

18. The method of claim 15, wherein analyzing the audio data comprises:
   determining a 3-dimensional vector magnitude of acceleration.

19. The method of claim 18, wherein identifying the wearer activity comprises:
   using data associated with a magnitude of the 3-dimensional vector magnitude of acceleration.

20. The method of claim 18, wherein identifying the wearer activity comprises:
   using data associated with a skewness of the magnitude of the 3-dimensional vector magnitude.

* * * * *